United States Patent [19]
Remacle et al.

[11] Patent Number: 5,939,383
[45] Date of Patent: Aug. 17, 1999

[54] CYCLIC PEPTIDES BEARING A TAIL DESIGNED FOR SUBSEQUENT CHEMICAL COUPLING AND PROCESS FOR PREPARING SAME

[76] Inventors: Jose Remacle, 14 Chemin des Pierres, B-5020, Malonne; Dominique Delforge, 22, Rue du Séminaire, B-5000 Namur, both of Belgium

[21] Appl. No.: 08/970,876

[22] Filed: Nov. 14, 1997

Related U.S. Application Data

[60] Provisional application No. 60/030,980, Nov. 15, 1996.

[51] Int. Cl.$^6$ .......................... A61K 38/00; A61K 38/12; C07K 5/00; C07K 7/00
[52] U.S. Cl. .................................. 514/9; 514/11; 530/317
[58] Field of Search ................................ 530/317; 514/9, 514/11

[56] References Cited

FOREIGN PATENT DOCUMENTS

| 150 199 | 8/1981 | Germany . |
| WO 95/21193 | 8/1995 | WIPO . |

OTHER PUBLICATIONS

Delforge et al, Analytical Biochemistry, vol. 242, pp. 180–186, 1996.

D. Delforge et al; "Solid–Phase Synthesis of Tailed Cyclic Peptides: The Use of α–allyl–protected Aspartic Acid Leads to Aspartimide and Tetramethylguanidinium Formation"; Letters in Peptide Science; vol. 3, No. 2; May 1996; pp. 89–97; XP–002063392.

M. Art et al; "Synthesis of Linear and Cyclic RGD–Peptides For The Purpose of Their Chemical Grafting On Poorly Adhesive Polymers Such as Polyethylene Terephtalate"; Polym. Preprints; vol. 36, No. 1; Apr. 1995; pp. 115–116; XP–002063393.

D. Delforge et al; "Automated solid–phase synthesis of cyclic peptides bearing a side–chain tail designed for subsequent chemical grafting"; Analytical Biochemistry; vol. 242, Nov. 15, 1996; pp. 180–186; XP–002063394.

S. A. Kates et al.; "Automated Allyl Cleavage for Continuous–Flow Synthesis of Cyclic and Branched Peptides"; Analytical Biochemistry; vol. 212; 1993; pp. 303–310; XP–002063395.

B. Ivanov et al.; "Synthesis and Use of a New Bromoacetyl–Derivatized Heterotrifunctional Amino Acid for Conjugation of Cyclic RGD–Containing Peptides Derived from Human Bone Sialoprotein"; Bioconjugate Chem.; vol. 6 1995; pp. 269–277; XP–002063396.

H.F. Brugghe et al; "Simultaneous Multiple Synthesis and Selective Conjugation of Cyclized Peptides Derived From a surface Loop of a Meningococcal Class 1 Outer Membrane Protein"; International Journal of Peptide and Protein Research; vol. 43; 1994; Copenhagen, Denmark; pp. 166–172; XP–002063397.

*Primary Examiner*—Avis M. Davenport
*Attorney, Agent, or Firm*—Knobbe, Martens, Olson & Bear LLP

[57] ABSTRACT

A cyclic peptide includes a dicarboxylic amino acid. The cyclic peptide bears at least one tail for subsequent coupling on a solid support, on a high molecular weight compound, on a marker, or on one or more other similar or different cyclic peptides. The present invention is also related to the preparation process of the cyclic peptide and to a biomaterial which includes the cyclic peptide.

21 Claims, 7 Drawing Sheets

CYCLIC PEPTIDES BEARING A TAIL DESIGNED FOR SUBSEQUENT CHEMICAL COUPLING AND PROCESS FOR PREPARING SAME

RELATED APPLICATION

The present application claims the benefit of priority under 35 U.S.C. § 119(e) of U.S. Provisional Application No. 60/030,980, filed Nov. 15, 1996.

FIELD OF THE INVENTION

The present invention is in the field of the biotechnology and relates to cyclic peptides designed for subsequent chemical grafting or coupling on a solid support, on a marker, on a high molecular weight compound and/or another cyclic peptide, and to their preparation process.

BACKGROUND OF THE INVENTION AND STATE OF THE ART

Peptides play a pivotal role in vivo because of their ubiquitous involvement in a variety of interactions with other biological molecules and proteins such as cell receptors, antibodies or enzymes. Although they are naturally flexible and can adopt a large number of different conformations, their biological activity is usually the result of one specific three-dimensional conformation. In laboratory experiments the conformation of peptides is also studied to reproduce specific determinants (epitopes) of high molecular weight proteins. The length of the peptides used for these studies is in general limited (up to fifteen amino acids) to overcome the problems that arise with increasing length of the peptide.

However, these peptides show a higher flexibility compared to the native protein. For this reason, their biological activity is usually lower than in the native conformation unless they are in some way rigidified. One way to achieve this is to synthesize different head-to-tail cyclic peptides with restricted conformational flexibility and to determine which of these analogs retains biological activity (Kessler H., 1982, Angew. Chem. Int. Ed. Engl., 21, 512–523; Kessler H et al., 1989, in Computer-aided drug design, methods and applications, Ed T. J. Perun and C. L. Probst, pp. 461–484, Marcel Dekker, New-York; Hruby V. J. et al., 1990, Biochem. J., 268, 249–262; Toniolo C., 1990, Int. J. Pept. Protein Res., 35, 287–300; Gilon C et al., 1991, Biopolymers, 31, 745–750).

Cyclic peptides can be formed in solution, in diluted conditions, by activation of a side-chain protected linear peptide using carbodiimide or diphenylphosphorylazide, followed by subsequent deprotection of the side-chains (Kessler H et al., 1989, in Computer-aided drug design, methods and applications, Ed. T. J. Perun and C. L. Probst, pp. 461–484, Marcel Dekker, New-York; Toniolo C., 1990, Int. J. Pept. Protein Res., 35, 287–300; Gurrath M. et al., 1992, Eur. J. Biochem., 210, 911–921; Izumiya N. et al., 1981, Biopolymers, 20, 1785–1791; Brady S. F. et al., 1983, in Peptides, Structure and Function, Proceedings of the Eighth American Peptide Symposium, Ed. V. J. Hruby and D. H. Rick, pp. 127–130, Pierce Chemical Company, Rockford, Illinois; He J. X. et al., 1994, Lett. Peptide Sci., 1, 25–30). Side-chain to side-chain cyclization has been achieved through lactam (Hruby V. J. et al., 1990, Biochem. J., 268, 249–262; Hoffmann E. et al., 1991, Liebigs Ann. Chem., 585–590) or disulfide bridge formation, between two cysteines incorporated in the sequence (Hruby V. J. et al., 1990, Biochem. J., 268, 249–262; Cavelier F. et al., 1989, Bull. Soc. Chim. France, 788–798). Cyclization of unprotected peptides has also been obtained by oxime formation in aqueous solution (Pallin T. G. and Tam J. P., 1995, J. Chem. Soc., Chem. Commun., 2021–2022). Although these methods have been widely used, they suffer from the fact that they are time-consuming and that side reactions like cyclodimerization, oligomerization or racemization of the C-terminal residue are difficult to avoid.

To overcome this problem, a fully automated synthesis procedure has been proposed, with the cyclization step occurring directly on the column (Kates S. A. et al., 1993, Anal. Biochem., 212, 303–310). This method allows the synthesis of cyclic peptides containing an acid (Asp, Glu) or an amide residue (Asn, Gln) (Kates S. A. et al., 1993, Anal. Biochem., 212, 303–310). In this method, an $\alpha$-allyl protected acid residue like Fmoc-Asp-OAl or Fmoc-Glu-OAl is incorporated as the first residue during the synthesis by fixation of its free carboxylic side-chain on the synthesis support. The peptidic chain is then elongated following the standard Fmoc synthesis procedure before specific cleavage of the $\alpha$-allyl protecting group, at the carboxyterminal end of the peptide, with palladium (0). Then the nucleophilic attack of the amino-terminal group of the peptide on the deprotected carboxylic end, allows the head-to-tail cyclization on the column (Kates S. A. et al, 1993, Anal. Biochem., 212, 303–310).

Other strategies incorporating (bromoacetyl) diaminopropionic acid in the sequence (Ivanov et al., 1995, Bioconjugate Chem., 6, 269–277) or bromoacetyl-beta-alanyl-lysine derivatives (U.S. Pat. No. 5,444,150) are also described in the scientific literature. Cyclization was for example obtained by covalent linkage between diaminopropionic acid and a cysteine residue of the sequence. This cyclization method was not automated and was achieved by a side-chain to side-chain link.

AIMS OF THE INVENTION

The present invention aims to provide cyclic peptides and their preparation process, which allow subsequent chemical grafting on coupling on said cyclic peptides, i.e. their attachment to a solid support, to a high molecular weight compound, to a marker and/or to other cyclic peptides, in order to provide new or improved biotechnological applications, particularly in the field of affinity chromatography, immunization, development of diagnostic tests, vaccines and pharmaceutical compositions, for Biacor experiments, for development of libraries of various conformational constrained peptides or for the development of new biomaterials which allow or improve the binding of specific antibodies, receptors, ligands, cells and tissues, for example.

SUMMARY OF THE INVENTION

The present invention is related to a cyclic peptide comprising a dicarboxylic amino acid, said cyclic peptide bearing at least one tail for subsequent coupling on a solid support, on a high molecular weight compound, on a marker and/or on one or more other (similar or different) cyclic peptides.

It is meant by a "cyclic peptide", a peptide comprising 4 or more amino acids (preferably between 4 and 15 amino acids) linked together to form a cycle, wherein at least one of said amino acids is a dicarboxylic amino acid.

However, the cyclic peptide according to the invention may also comprise amino acids which are coupled or grafted to other chemical compounds, such as saccharides (polysaccharides, oligosaccharides or monosaccharides, which may be made of glucose, fructose, mannose, fucose and/or ribose units).

Advantageously, the dicarboxylic amino acid included in the cyclic peptide according to the invention is a (D or L) glutamic acid or a 2-aminoadipic acid (D or L).

It is meant by a "tail", a chain or an arm made of chemical compounds, which allows the coupling of the cyclic peptide according to the invention on a solid support, on a high molecular weight compound, on a marker and/or on other cyclic peptides.

Advantageously, said tail can be branched in order to obtain the coupling of the cyclic peptide to several solid supports, several high molecular weight compounds, several markers and/or several cyclic peptides.

It is meant by "a high molecular weight compound", a molecule such as a protein carrier (BSA, KLH, lysosyme) having a molecular weight higher than 5 KD.

It is meant by "a marker", any chemical compound, such as a fluorescent chemical compound, a radioactive compound, which allows the specific identification of the cyclic peptide according to the invention.

According to a preferred embodiment of the present invention, the tail of the cyclic peptide is made of amino acids units such as cysteine, lysine, aspartic acid or glutamic acid, possibly separated by one or more spacers.

It is meant by a "spacer between the various amino acids units of the tail", one or more organic compounds which can link two or more amino acids such as amino acids having the formula $-NH_2-alkyl-COOH$ or $-NH_2-aryl-COOH$. Preferably, said spacer is a 6-amino-hexanoil.

The amino acids present in the cycle of the cyclic peptide according to the invention are natural amino acids or non-natural amino acids (other amino acids than the 20 amino acids used in the build up of natural proteins).

Preferably, said amino acids of the cycle of the cyclic peptide according to the invention are building blocks such as the ones described by James G. L. et al. (1993, Sciences, 260, 1937–1942), William B. J. et al. (1993, J. Med. Chemistry, 31), Ward P. et al. (1990, J. Med Chemistry, 33, 1848) or templates as described by Jackson S. et al. (1994, J. Am. Chem. Soc., 116, 3220–3230) used for the synthesis of peptidomonomers.

According to a specific embodiment of the present invention, the cyclic peptide according to the invention comprises in its cycle a sequence which mimics one binding sequence of a growth factor, preferably the sequence EQIM-RIKPHQ (SEQ ID NO: 1).

The present invention is also related to the solid support coupled to the cyclic peptide according to the invention. Preferably, said solid support is selected from the group consisting of a chromatographic gel (of a chromatography column), beads, the surface of any container such as a multiwell plate, preferably an ELISA polystyrene multiwell plate, or any other solid support which can be used for the culture of cells.

Another aspect of the present invention is related to the high molecular weight compound such as a protein carrier (for example BSA, KLH or lysozyme) coupled to the cyclic peptide according to the invention.

Another aspect of the present invention is related to the biomaterial comprising the high molecular and/or the solid support coupled to the cyclic peptide according to the invention, which allows adhesion, preferably a selective adhesion, of specific cells and/or tissues. Said biomaterial comprising said cells and/or tissues grafted or fixed upon the cyclic peptide according to the invention, and which can be incorporated into a biosensor, a bioreactor, an artificial organ or an artificial tissue.

According to the composition of the various amino acids of the cycle of said cyclic peptide, said biomaterial according to the invention can be used for the grafting or binding of specific antibodies, receptors, ligands, cells or tissues, and may be used for the production or the identification or known or new drugs, vaccines, hormones, interferons, cytokines, etc.

The biomaterial according to the invention may also be used for the screening of specific cells, in particular for the diagnostic of tumor cells, which may adhere differently than the normal cells upon the various types of the biomaterial according to the invention.

The cells or tissues described above can be of vegetable, animal and fungal origin, or can be unicellular microorganisms.

The biomaterial according to the invention can also be used to allow preferential cells and/or tissues adhesion on specific parts of the biomaterial in order to guide the cells and tissue growth along preferential directions, particularly for specific applications such as nerve reconstruction.

It is clear that the biomaterial according to the invention may also comprise specific mediums or compounds, such as extra-cellular matrix proteins or a portion thereof, which allow the proliferation of specific cells or tissues upon said biomaterial.

Examples of extra-cellular matrix proteins are collagen, laminiin, fibronectin, fibrin, chondronectin or a mixture thereof, as described in the International Patent Application WO96/09372, incorporated herein by reference.

The biomaterial according to the invention may also comprise specific mediums well known by the person skilled in the art and which will allow the survival and/or the proliferation of specific cells upon the biomaterial according to the invention (for instance, DMEM medium obtained from Bio Whittacker, which allows the proliferation of Schwann cells, the William's E medium obtained from Sigma, which allows the proliferation of hepatocytes, etc.).

The solid support of the biomaterial according to the invention can also be a microporous polymeric membrane covered upon one or both of its sides by one or more different cells strains in a specific nutritive medium, such as the "system" described in the International Patent Application WO96/09372, incorporated herein by reference.

A last aspect of the present invention is related to the process for the preparation of the cyclic peptide according to the invention, which is advantageously obtained by chemical synthesis using an automatic peptide synthesizer, preferably by a chemical synthesis directly on a solid support or a high molecular weight compound.

Preferably, in the method according to the invention, the washing conditions comprise the use of dichloromethane as a solvent in the presence of an aminated base in an additional washing step, after the steps of allyl cleavage and palladium wash.

Alternatively, the cyclization of the peptide could be achieved by replacing the Fmoc-Glu-Oal compound by Fmoc-Glu-ODmab and performing the cleavage step of Dmab protecting groups by lowing 2% hydrazine monohydrate in DMF through the resin (60 minutes) and subsequent washing of the resin with 8% DIEA in DMF. The resin cyclization was achieved by treatment of the resin either with diisopropylcarbodiimide (DIPCDI)/HOAE/DIEA in a fourfold excess for 2×18 hours, or with PyAOP/DIEA (fourfold excess) for 2×5 hours.

The present invention will be described in several non-limiting examples in reference to the following figures.

SHORT DESCRIPTION OF THE DRAWINGS

The FIG. 1 represents schematically the method used for automated synthesis of the tailed-cyclic peptide cyclo[-D-Val-Arg-Gly-Asp-Glu(-εAhx-Cys-NH$_2$)-] (SEQ ID NO:2) (allyl deprotection=Palladium(0) in acetic acid 5%/NMM 2.5%/chloroform (syringe 3); Palladium wash=DIEA 0.5%/sodium diethyldithio-carbamate 0.5%/DMF (auxiliary bottle); Additional washing=DIEA 8% in CH$_2$Cl$_2$ (wash 2 bottle); Fmoc cleavage=Piperidine 20% in DMF (deblock bottle); Cyclization on column=TBTU, BOP or HATU 0.3M in DIEA 8%/DMF (syringe 2); Peptide-resin cleavage=TFA:thioanisole: ethanedithiol:anisole (90:5:3:2)).

The FIG. 2 represents a reversed-phase HPLC profile of the crude product obtained after synthesis of the tailed cyclic peptide cyclo[-D-Val-Arg-Gly-Asp-Glu(-εAhx-Cys-NH$_2$)-] (SEQ ID NO:2) according to FIG. 1 with an additional washing step after the Palladium wash (A. Manual washing step and cyclization with HATU (3 rounds of 60 minutes); B. Automatic additional washing step and cyclization with TBTU reagent (2 rounds of 3 hours); C. Automatic additional washing step and cyclization with HATU reagent (2 rounds of 60 minutes). Molecular weight of eluting compounds (ESI-MS):(4) =771;(10)=1543.6).

The FIG. 3 represents the grafting of $^{125}$I-labelled tailed cyclic peptide on aminated PET, with (gray histograms) or without (white histograms) SMCC as coupling reagent (CTL=grafting on native (unmodified) PET films; test= grafting on aminated PET films).

The FIG. 4 represents a (A) schematic representation of the method used for grafting tailed cyclic RGD peptides on BSA, its adsorption on polystyrene plates and its use for adhesion assays, and (B) a schematic representation of the method used for grafting tailed cyclic RGD peptides on BSA after it has been adsorbed on the polystyrene plate.

The FIG. 5 shows the results of the adhesion of endothelial cells on reconditioned polystyrene support as described in FIG. 4A (the albumin was first grafted with the tailed cyclic RGD peptide before being adsorbed on the plate. The assay was performed on fibronectin coated plates (FN), on BSA coated plates (BSA), on BSA coated plates grafted with cysteine (BSA-CYS), with a cyclic RGD peptide (BSA-T26)).

The FIG. 6 shows the results of the adhesion of endothelial cells on reconditioned polystyrene supports as described in FIG. 4B (the assay was performed on fibronectin coated plates (FN),on polystyrene (PS) on BSA coated plates (BSA), on BSA coated plates grafted with cysteine (BSA-CYS), with a linear RGD peptide (BSA-P21), with a cyclic RGD peptide (BSA-T26) or with a cyclic DRVG peptide (BSA-T29). Adhesion of the cells was estimated after 15 minutes incubation using a colorimetric assay).

The FIG. 7 shows the results of same experiment as in FIG. 6 wherein the peptides were directly adsorbed on the BSA-coated plates without coupling reagent.

The FIG. 8 represents the structure of a dimeric tailed cyclic peptide which mimic vascular endothelial growth factor (VEGF) and could act as agonist of this growth factor for the binding to KDR receptor.

DETAILED DESCRIPTION OF THE INVENTION

Figure 1:
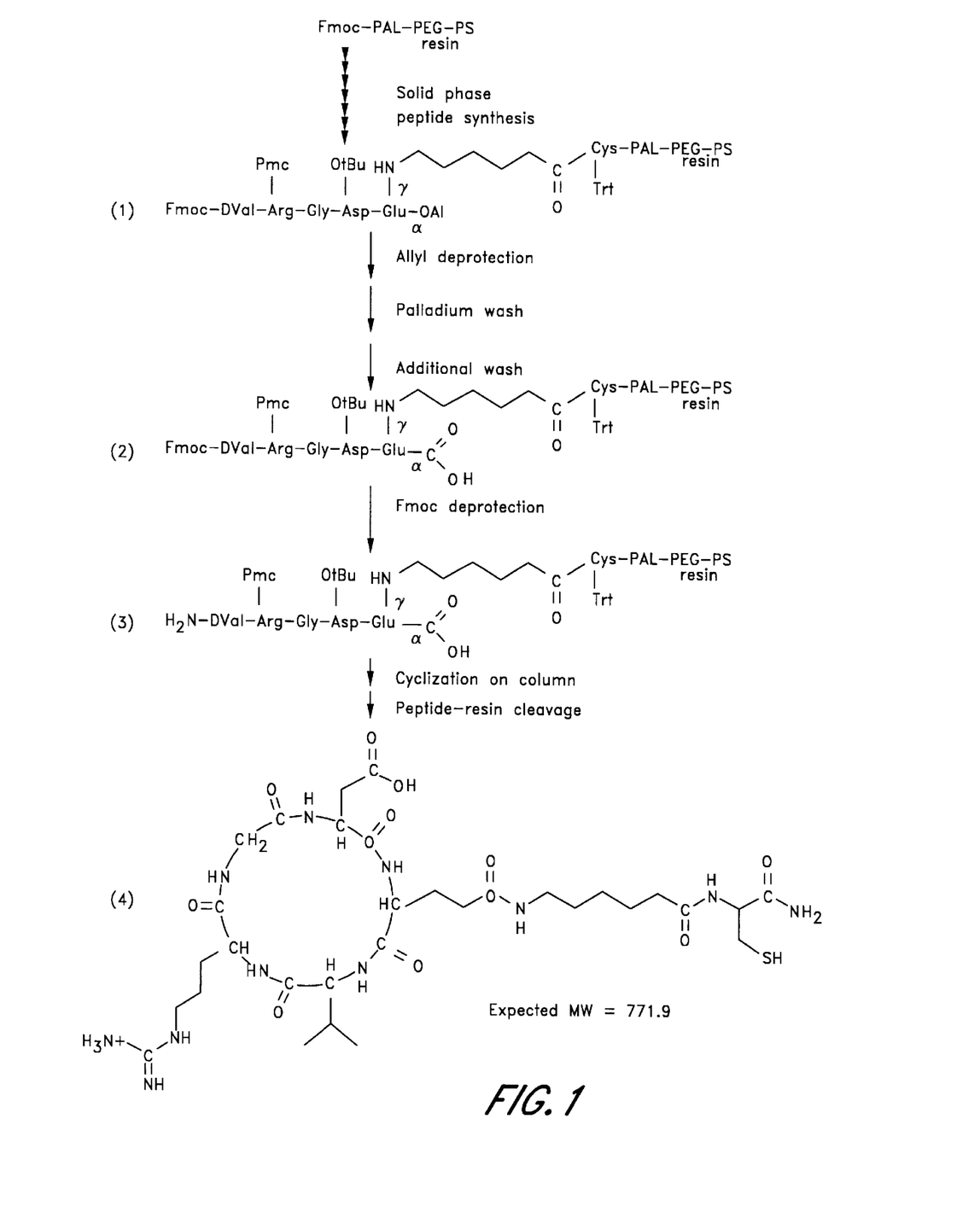

The tailed cyclic peptide according to the invention is a peptidic sequence which contains a dicarboxylic amino acid, like glutamic acid, which is linked in the peptidic cycle part of the peptide by its a-carboxylic and amino group, and bears the anchoring tail on its side-chain carboxylic group. One example is given in FIG. 1 which summarizes the procedure followed to obtain a five amino acid peptide cyclo(-D-Val-Arg-Gly-Asp-Glu-) (SEQ ID NO:3) with as anchoring tail 6-aminohexanoid acid and cysteine. The choice of this tail composition is based on the fact that the 6-aminohexanoic acid introduces a 6 atom long tail which is usually sufficient to allow the peptide to be far enough from the solid support and to be recognized by a binding constituent like a receptor, an antibody, etc. If necessary other amino acids or longer chains can be incorporated in the arm in the same way. The cysteine comprises a free thiol group which can be used as reactive function for further grafting on solid support like amine group in the presence of SMCC. Similarly, other amino acid molecules can be incorporated in said side chain tail in order to obtain a longer arm, more hydrophobic or more hydrophilic or to introduce specific chemical groups.

The use of the carboxylic amino acid like the glutamic acid as the amino acid in the crossroad between the cyclic peptide and the anchorage tail is a key to the success for this invention. Unexpectedly, it can not be replaced by aspartic acid as it is the case for the formation of single cyclic peptide without tail. Indeed, in a first set of experiments, the Inventors have tried to obtain the synthesis of the tailed cyclic peptide cyclo[-D-Val-Arg-Gly-Asp-Asp(-εAhx-Cys-NH$_2$)-] (SEQ ID NO:4), with the protocol developed for the simple cyclic peptides (Kates et al, 1993, Anal. Biochem., 212, 303–310), incorporating Fmoc-L-Asp-OAl as cyclizing amino acid. We note that εAhx refers to 6-aminohexanoic acid. The method failed to give the expected product as more than five different compounds were identified in the crude product. However, the same method provided excellent results for the preparation of the simple cyclic analogue cyclo[-D-Val-Arg-Gly-Asp-Asn-] (SEQ ID NO:5) which only differs by the absence of the anchoring side-chain tail -εAhx-Cys-NH$_2$.

The analysis of the products obtained has shown that the aspartic acid incorporated in the sequence at the N-terminus of 6-aminohexanoic acid leads to the undesired side reaction of aspartimide formation in the presence of piperidine. This aspartimide formation on the aminoterminus of 6-aminohexanoic acid has not yet been described, especially with the allyl protecting group.

Furthermore, the formation of the aspartimide ring led to a product with the same molecular weight as the expected cyclic peptide, and prevented the reaction of the free terminal amino group for cyclization. This allowed additional side reactions to occur during the last step of the synthesis such as N-terminal acetylation or tetramethylguanidium formation by TBTU treatment.

These side reactions indicates that aspartic acid is unsuitable for the synthesis of tailed cyclic peptides. In a second set of experiments, the Inventors have replaced the aspartic acid by the glutamic acid. The synthesis of cyclo[-D-Val-Arg-Gly-Asp-Glu(-εAhx-Cys-NH$_2$)-] (SEQ ID NO:2) was performed according to the method of the invention, using Fmoc-L-Glu-OAl as cyclizing amino acid. Surprisingly, this method also failed to give satisfying results, as the expected product (M$_r$=771.3; R$_t$=19.6 min) was largely contaminated by side reaction products. Most of these side products had a higher hydrophobicity and a higher molecular weight than 5 KD, except the product eluting at $R_t$=10.6 minutes which was found to be 1-hydroxybenzotriazole (HOBt). The use of BOP instead of TBTU as cyclizing reagent gave essentially the same HPLC profile without HOBt. In another experiment, an additional manual washing step, including DMF, CHCl$_3$, methanol, CH$_2$Cl$_2$, 8% DIEA in DMF, 8% DIEA in CH$_2$Cl$_2$, was introduced in the synthesis protocol after palladium wash and Fmoc removal. This resulted in an improved crude product with the expected tailed cyclic peptide as major product of the reaction ($M_r$=771; $R_t$=19.6) and a minor side product corresponding to the dimeric form of the peptide ($M_r$=1543.6; $R_t$=30.2 min). This indicated that the side products obtained in the first trials with Fmoc-L-Glu-OAl were the result of an incomplete washing of the resin during the last steps of the synthesis (allyl palladium cleavage and Fmoc removal). According to these experiments, the side reaction, identified as N-terminal acetylation, can be due to the presence of acetic acid in the solubilization solution of palladium(0) which is used for the allyl cleavage and which was probably not completely removed during the subsequent steps of the synthesis. Furthermore, after the final Fmoc removal (step (3) in FIG. 1), the carboxylate of the peptide is left as a piperidine salt which can be converted to piperidine amide under the coupling conditions of the cyclization step, adding +67 Da to the linear peptide. When the additional washing step was included in the protocol a non competitive cyclization was obtained.

Figure 2A:
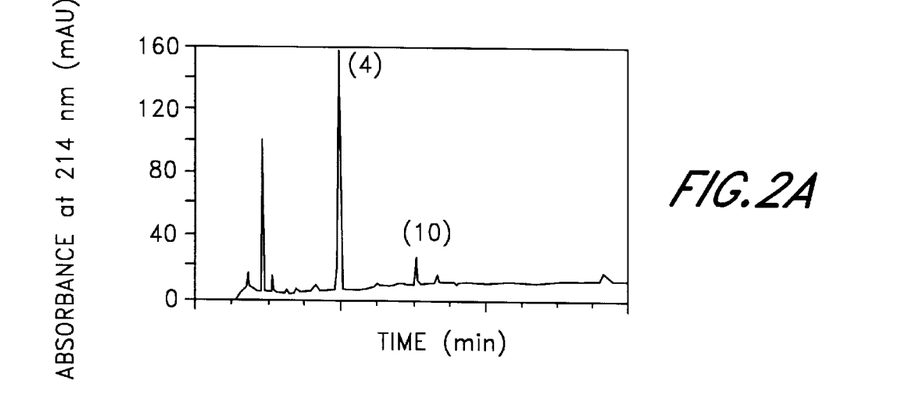
Figure 2B:
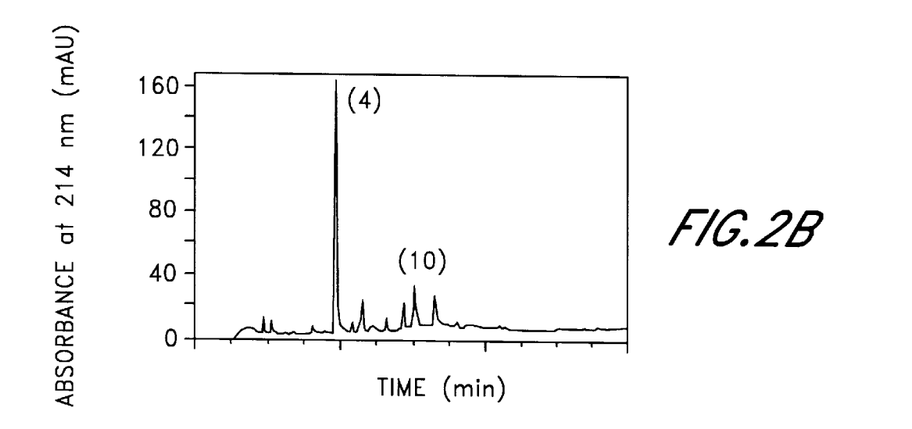

The procedure was adapted for automatic synthesis on the PerSeptive Biosystems 9050 Plus peptide synthesizer. Among the different washing conditions tested in the manual protocol, one selects the combined effect of solvent changing (dichloromethane in place of DMF) with the presence of an aminated base (DIEA 8%). These washing conditions were tested for the synthesis of cyclo[-DVal-Arg-Gly-Asp-Glu(-εAhx-Cys-NH$_2$)-] (SEQ ID NO:2) using TBTU (2 rounds of 3 hours) or HATU (2 rounds of 60 minutes) as cyclization reagents. The HPLC profile of the crude products presented in FIGS. 2A and 2B show only one main peak as for the manual washing. There is still very small amount of contaminating products which are lower when HATU was used for cyclization (FIG. 2B) compared with TBTU (FIG. 2A). The yield obtained in these conditions was above 85% for the crude product and around 40% after purification.

The reason why such secondary products were obtained during the cyclization step of the tailed cyclic peptides, and not in the case of simple cyclic peptides, is still an open question, but this was systematically observed for different independent syntheses. Incomplete removal of acetic acid was also observed during the synthesis of the tailed cyclic peptide cyclo[-DVal-Arg-Gly-Asp-Asp(-εAhx-Cys-NH$_2$)-] (SEQ ID NO:4), giving rise to N-acetylated linear peptides with a molecular weight 42 kD higher than expected (Delforge D. et al., 1996, Lett. Pept. Sci., 3, 89–97). It is known that the formation of peptide secondary structures like b-sheets can be a major factor for the formation of impurities during solid-phase synthesis (Hyde C. et al., 1994, Int. J. Pept. Prot. Res., 43, 431–440). One can not exclude the formation of similar secondary structures during the synthesis of complex molecules like tailed cyclic peptides, and the possible interaction of these structures with some of the reagents which would then be difficult to remove with the standard washing steps of the procedure. If it is the case, this would explain the results obtained and the improvement achieved with the method of the invention.

A cyclic peptide bearing a side chain tail can be obtained if the D-isomer of glutamic acid is used or another dicarboxylic amino acid with a longer side chain than glutamic acid, like the 2-amino adipic acid (D or L). Also the first or a subsequent amino acid which is incorporated during the synthesis of the peptide and which after release from the support will serve for further grafting can be any amino acid with function suitable for such use. This is the case for the amino group of lysine is used or the carboxyl group if aspartic or glutamic acid is used. These functional amino or carboxyl groups are easy to bind on activated support or proteins. These tailed cyclic peptides are ready-to-use for chemical grafting in various applications like the development of new biomaterials for improved cell adhesion, affinity chromatography, immunization, vaccine development, ELISA kits or for building libraries of conformationally constrained peptides.

Figure 3:
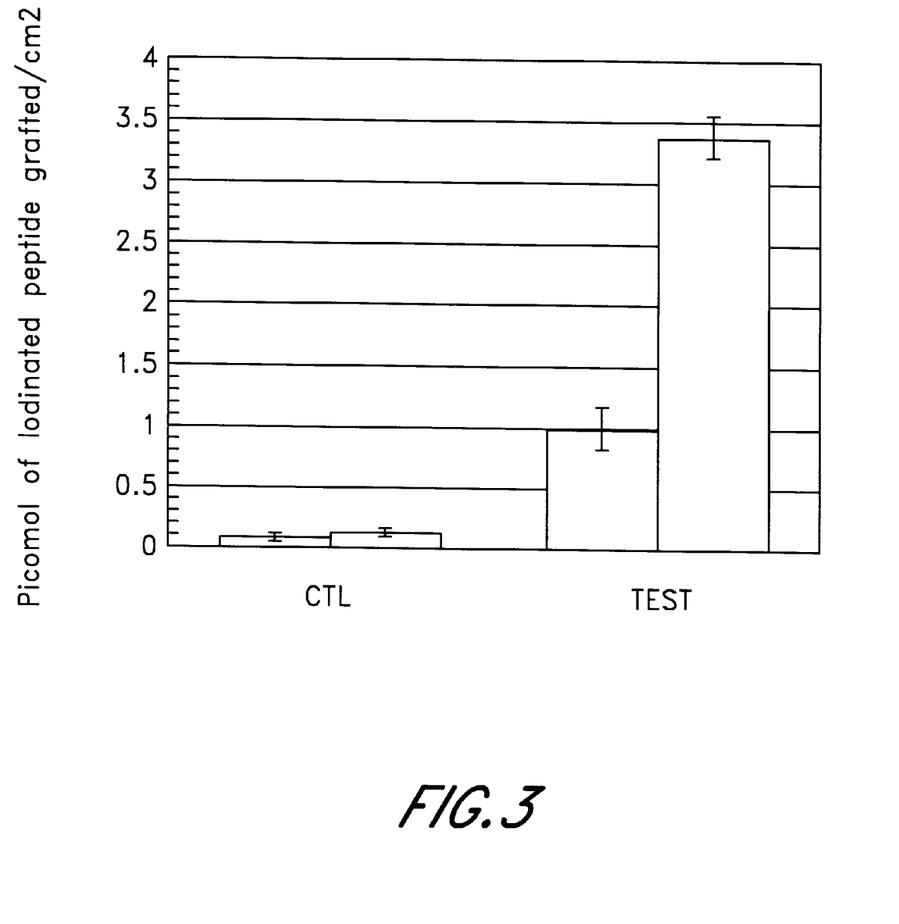
Figure 5:
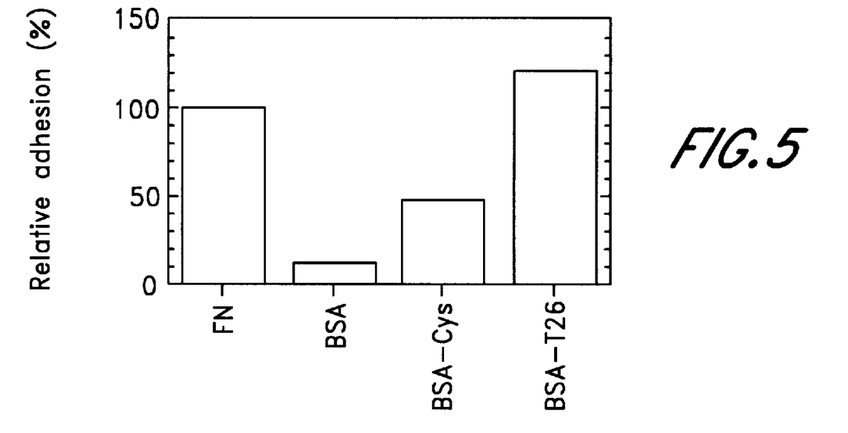
Figure 6:
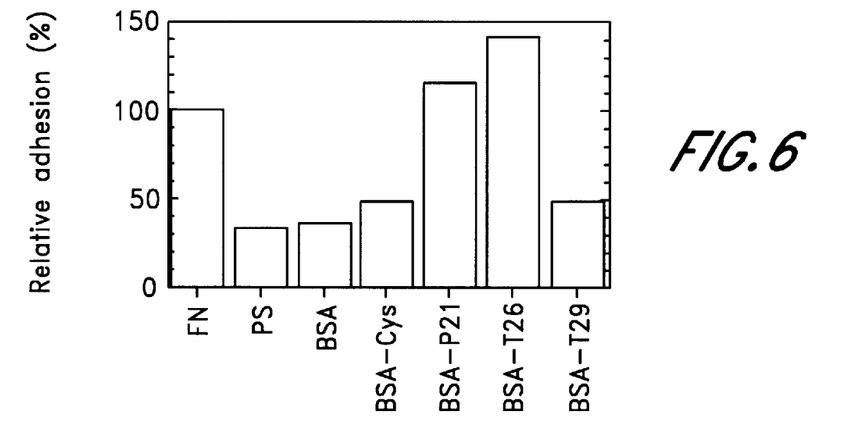
Figure 7:
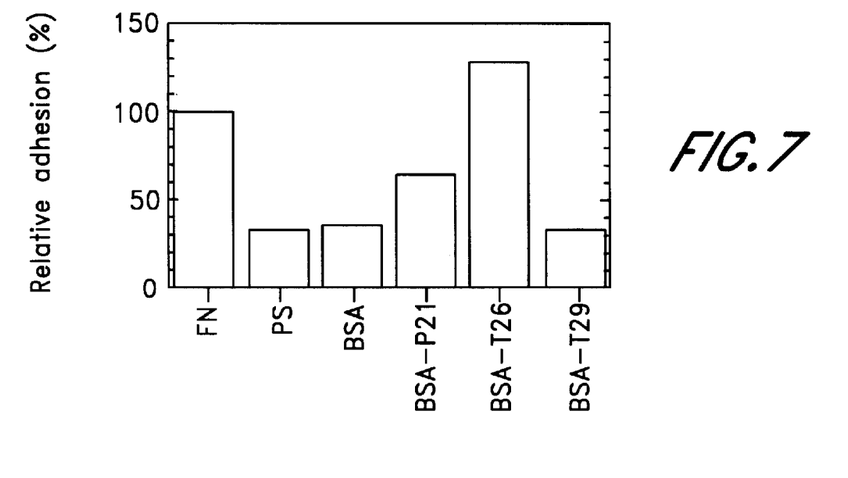
Figure 8A:
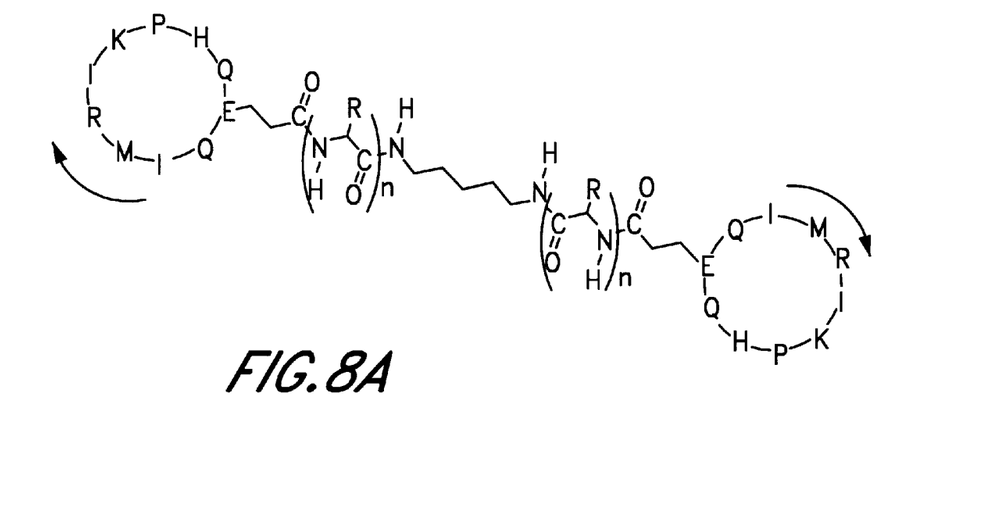
Figure 8B:
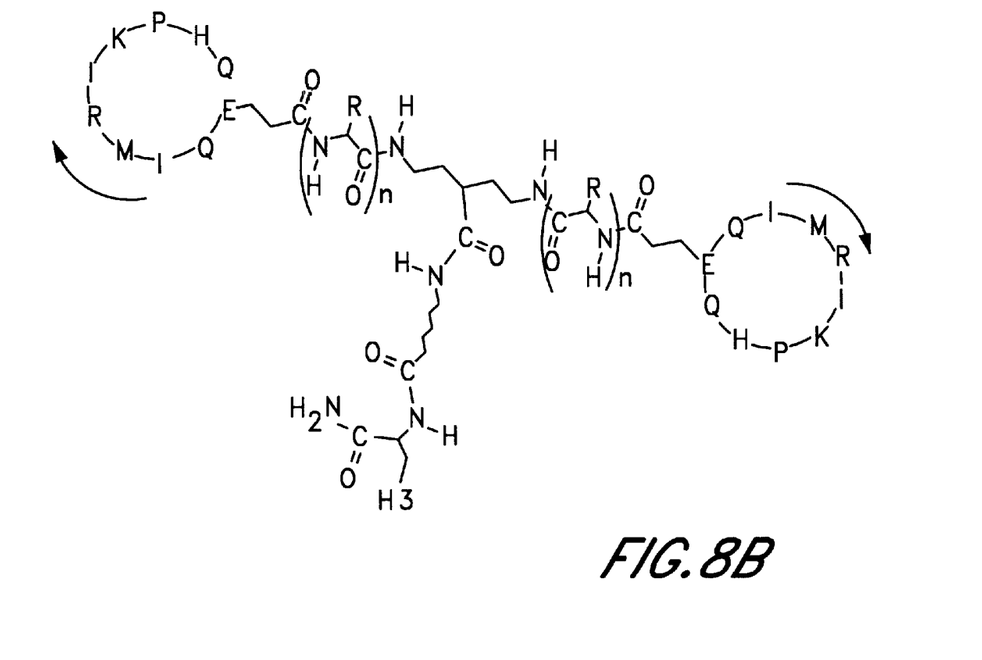

A cyclic peptide bearing a RGD motif grafted on aminated poly(ethylene terephtalate) is given in the example 1 (FIG. 3). In the example 2 (FIGS. 4, 5 and 6), said tailed cyclic peptide is grafted on bovine serum albumin coated on polystyrene plates can serve as anchorage for the adhesion of cells. In these experiments, the tailed cyclic peptide was grafted on the BSA either before adsorption of the BSA on the plate (FIGS. 4A and 5) or after its adsorption on the plate (FIGS. 4B and 6). In one experiment, the tailed cyclic peptides were directly adsorbed on the BSA without any covalent coupling on the protein (FIG. 7). These examples can be extended to any ligand which binds to a receptor. A peptide can be defined which mimics the ligand binding structure and which can take the place of the ligand on the receptor or enzyme binding site, and in this way obtain the desired biological response. This is especially useful for the preparation of biomaterial compatible with living cells. Such cyclic tailed peptides can also be constructed from non natural amino acids or using building blocks which can be incorporated in the amino acid sequence The design of the peptide can also affect the cell behavior, for example leading to a pro-adhesive surface as shown in example 2 for the tailed cyclic RGD peptide. However, other peptides could have different effects on cells. For example, REDV (SEQ ID NO:6) would be pro-adhesive, DGEA (SEQ ID NO:7) would be anti-adhesive, while SFLLR (SEQ ID NO:8) would enhance activation of cells, and ANFLVWEIVRKKP (SEQ ID NO:9) would lower the activation of cells. Other peptides like TLEGTKKGHKLHLDYIGP (SEQ ID NO:10) would be pro-proliferative, mainly due to the GHK amino acids, while GHE and GHP would have anti-proliferative effects on endothelial cells.

One particular application of tailed cyclic peptides is to construct dimeric cyclic peptides using the tail for linking two peptides together. This is a particularly easy way to obtain dimeric cyclic peptides. The application of such construct are numerous. The most interesting is to obtain an agonist effect once the dimer is linked to the corresponding dimeric receptor. Indeed many receptors are active only in a dimeric form and this can be obtained with such dimeric cyclic peptide.

A peptidic tail can also be added to this cyclic dimeric peptide for its fixation on a support or a macromolecule such as a protein. Multimeric peptides can also be constructed in the same way by linking the tail of a cyclic peptide to the cyclic part of a second tailed cyclic peptide, leaving the tail of the second peptide free for another linking. An alternative is to provide on the peptide two tails ready for further linking.

The peptide sequence which is responsible for the binding of growth factors on their receptors is often known, and these peptides can advantageously be used as tailed cyclic peptides. For example, the CYAAPLKPAKSC (SEQ ID NO: 11) and CGTGYGSSSRRC (SEQ ID NO:12) are two peptides which can fix on the IGF-1 receptor. APSGHYKG (SEQ ID NO:13) and KRTGQYKL (SEQ ID NO:14) are specific for the bFGF receptor; ANFLVWEIVRKKP (SEQ ID NO:15) is specific for PDGF, and we propose a cyclic EQIMRIKPHQ (SEQ ID NO:16) for the receptor KDR of VEGF. These peptides can have antagonist effect when used as monomers, but agonist when dimeric as explained here above. An agonist effect of peptide mimicking the VEGF can be particularly useful for preparing biomaterial substitute for blood vessels since they could speed up the anchorage and the growth of endothelial cells, protecting this surface from platelet aggregation and other pro-inflammatory reactions. A proposed dimeric cyclic peptide with a tail ready for grafting on a polymeric surface is presented in FIG. 7.

EXAMPLE 1

General Description Of The Preparation Process
Materials

Fmoc-protected amino acids and reagents, including Fmoc-L-Glu-OAl, Fmoc-PAL-PEG-PS and solvents used for the synthesis were purchased from PerSeptive Biosystems (Watford Herts, UK). HATU used for on-line cyclization was a generous gift of PerSeptive Biosystems. Alternatively, some protected amino acids and TBTU coupling reagents were obtained from Neosystem Laboratoire (Strasbourg, France). All amino acids were used as free acids and activated just before coupling using TBTU. Except when otherwise mentioned in the text, tBu was used for side chain protection of Asp, while Trt and Pmc were used respectively as side chain protecting groups for Cys and Arg. All other reagents required for washings, cleavage and purification were obtained from Acros Chimica (Beerse, Belgium) except acetonitrile from Carlo Erba (Milano, Italy), N,N-dimethylformamide and diethylether from Labscan (Dublin, Ireland), tetrakis-(triphenylphosphine)-palladium(0) from Aldrich Chemical Company (Milwaukee, Wis.) and anisole from Sigmna Chemical Company (St Louis, Mo.). All solvents were of HPLC grade or equivalent quality and were used without further purification except for TFA and dichloromethane which were p.a. grade and were redistilled before use.

Peptide Synthesis by Standard Chain Elongation

Automated continuous-flow solid-phase peptide synthesis was performed following a standard Fmoc protocol (Atherton E., and Sheppard R. C., 1989, Solid Phase Peptide Synthesis. A Practical Approach, IRL Press at Oxford University Press, Oxford) on a PerSeptive Biosystems 9050 Plus PepSynthesizer. The synthesizer was set in the "Allyl mode" which allows the synthesis of linear, branched or cyclic peptides (Kates S. A. et al., 1993, Anal. Biochem., 212, 303–310). All amino acids were incorporated as free acids using TBTU as coupling agent (Knorr R. et al., 1989, Tetrahedron Lett., 30, 1927–1930), without addition of HOBt which is not required for TBTU activation. The typical protocol used for standard chain elongation was as follows: Fmoc deprotection with 20% piperidine in DMF (7 min), DMF washing (7 min), extended amino acid coupling (60 min), and DMF washing (4 min). The pump flow rate was 5 ml/min. Syntheses were carried out on a Fmoc-PAL-PEG-PS resin (0.4 to 1.2 g; substitution 0.16 mmol/g) (Albericio F. et al., 1990, J. Org. Chem., 55, 3730–3743) available from PerSeptive Biosystems, with a four-fold excess of Fmoc-amino acid and TBTU. TBTU was directly added as a solid in the amino acid vials and dissolved to a final concentration of 0.3M with a solution of DIEA 8% in DMF just before coupling. Syringe 2 of the synthesizer was used for this purpose.

Figure 2C:
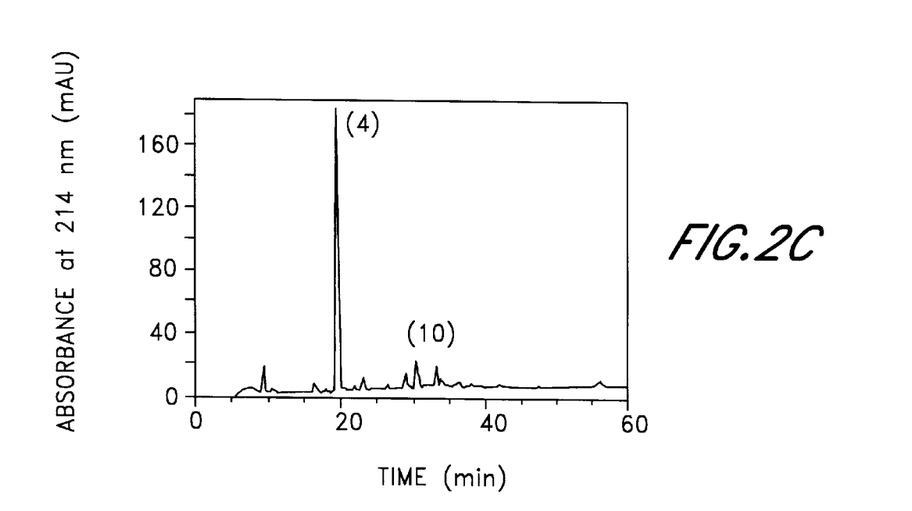

For the synthesis of TCP a protected Fmoc-cysteine was incorporated as the first amino acid of the sequence (FIG. 2) to allow subsequently end point grafting if required. Fmoc-6-aminohexanoic acid was then incorporated as the second amino acid of the sequence to introduce a 6-carbon spacer between the anchoring cysteine of the tail and the cyclizing amino acid residue of the peptidic cycle (FIG. 2). An α-allyl-protected Fmoc-glutamic acid residue Fmoc-L-Glu-OAl was coupled via its free carboxylic side-chain as third amino acid to allow cyclization to occur at the final step of the synthesis. The rest of the sequence elongation was achieved following standard Fmoc peptide synthesis, before allyl deprotection (2) and peptide cyclization (4) (FIG. 2).

Automated Allyl Deprotection and Improvement of Washing Conditions After Palladium Treatment Side chain removal of the allyl group was performed automatically on the column following the method previously described by Kates et al for automated synthesis of cyclic peptides (Kates S. A. et al., 1993, Anal. Biochem., 212, 303–310). Pd(PPh$_3$)$_4$ used as catalyst (2 meq/meq of peptide) was stored in the amino acid rack after the last amino acid of the sequence. Syringe 3 of the synthesizer was used to dissolve the palladium catalyst to a final concentration of 0.07M with a solution of 5% HOAc and 2.5% NMM in CHCl$_3$. After 2 h of recirculation through the column, this solution was washed with a solution of 0.5% DIEA and 0.5% diethyldithiocarbamate in DMF (auxiliary bottle, 12 min, 6 ml/min) and with DMF (10 min, 6 ml/min) to prepare the support for the final cyclization step. In the final synthesis experiments an additional wash cycle with DIEA 8% in CH$_2$Cl$_2$ (wash 2 bottle, 12 min, 6 ml/min) was introduced for complete removal of reagents and side products resulting from allyl deprotection and palladium wash. The program of the software in "Allyl Mode" and "MCPS Mode" was adapted accordingly.

Automated Cyclization

After the linear synthesis and allyl deprotection, the N-terminal Fmoc protecting group was removed by piperidine treatment (20% in DMF, 7 min) and the resin was washed with DMF (7 min, 7 ml/min). The cyclization was achieved on the column by using a four-fold excess of coupling agent during different periods of time. Both TBTU (2×3 h) (Atherton E., and Sheppard R. C., 1989, Solid Phase Peptide Synthesis. A Practical Approach, IRL Press at Oxford University Press, Oxford), BOP (2×3 h) (Castro B. et al., 1975, Tetrahedron Lett., 1219–1222) and HATU (2×60 min) (Carpino L. A. et al., 1994, J. Chem. Soc. Chem. Commun., 201–203) have been tested as cyclization activators, without HOBt, as previously mentioned. Four equivalents of activator, stored in the amino acid vial positioned after the one containing the palladium catalyst, were dissolved to a final concentration of 0.3 M with a solution of DIEA 8% in DMF from syringe 2. The solution was delivered to the allyl-deprotected peptide support and was allowed to recirculate during a time long enough to obtain complete cyclization. This step was usually repeated a second time with fresh activator to be sure to achieve a complete cyclization. This was checked by the Kaiser ninhydrin test (Kaiser E. T. et al., 1970, Anal. Biochem., 34, 595–598) with an increased revelation time (15 min at 100° C.) to compensate for the poor sensitivity of the test on PEG-PS beads. Finally, the resin was washed with DMF (4 min, 7 ml/min).

Cleavage Conditions

The peptide-resin was removed from the column, washed with methanol, dichloromethane and dried under vacuum. Cleavage was achieved by treatment with reagent R (Albericio F. et al., 1990, J. Org. Chem., 55, 3730–3743) i.e. TFA-thioanisole-ethanedithiol-anisole (90:5:3:2) for 2 h. The filtrate was collected and the resin was further washed with TFA. After evaporation of the solution under high vacuum, diethylether was added to the dry residue and cooled to −20° C. to precipitate the peptide. The supernatant was removed and cold diethylether was further added to repeat the washing step up to five times, followed by extractions in biphasic water-ether (50:50) systems if necessary. The aqueous solution obtained was then lyophilized after addition of some drops of glacial acetic acid, to maintain the free thiols in their reduced state.

Characterization of the Synthesis Product

Peptide purity was determined by reversed-phase HPLC on a Nucleosil $C_{18}$ column (250 mm×4 mm) from Macherey-Nagel (Düren, Germany). The HPLC system was a Hewlett Packard HP 1090 Liquid Chromatograph equipped with a programmable wavelength diode array detector HP 1040 M Series II, set at 214 and 270 nm. Analyses were performed at a flow rate of 1 ml/min with a linear gradient of solvent A to solvent B, from 10% B (at t=3 min) to 50% B (at t=60 min), were A was TFA 0.1% in $H_2O$ and B was TFA 0.1% in $CH_3CN$-$H_2O$ (80:20). Samples were solubilized in solvent A at a concentration of 1 mg/ml. Injection volume was 50 ml. Molecular weights were determined by high performance liquid chromatography/mass spectrometry (HPLC-MS) (Heath T. G. and Giordani A. B., 1993, J. Chromatogr., 638, 9–19; Wang R., and Chait B. T., 1994, Curr. Opin. Biotechnol., 5, 77–84) on a Kontron Instruments HPLC 325 System connected to a uv-detector Kontron 332 and a Fisons Instruments VG platform II electrospray ionisation mass spectrometer (ESI-MS).

EXAMPLE 2

Grafting of Tailed Cyclic Peptides on Aminated Poly(ethyleneterephtalate)

Poly(ethyleneterephtalate) (PET) film samples (diameter 1.2 cm) were first carboxylated by hydrolysis in 0.25N NaOH and acetonitrile (1:1; V/V) and subsequent oxidation with permanganate according to Marchand-Brynaert et al (1995, J. Colloid Interface Sci., 173, 236–244). Carboxylated PET was then aminated according to the method of Zammatteo et al (1996, Anal. Biochem., 236, 85–94) using ethylenediamine instead of N-methyl-1,3-propane diamine to introduce primary amino groups on the support. The tailed cyclic peptide cyclo[-DVal-Arg-Gly-Asp-Glu(-εAhx-Tyr-Cys-$NH_2$)-] (SEQ ID NO:17) was iodinated with $^{125}I$ according to Greenwood et al (1963, Biochem J., 89, 114–123) and grafted on the aminated PET using N-succinimidyl 4-(N-maleimidomethyl)cyclohexane-1-carboxylate (SMCC) as bifunctional reagent. Samples of aminated PET were incubated 30 min at 30° C. under shaking in 3.7 mM SMCC 100 mM $NaH_2PO_4$ pH 7.0 10% DMSO (2 ml/sample). Activated support was washed 3×5 min with $NaH_2PO_4$ pH 6.0 and incubated 20 hours at room temperature under shaking in the presence of a $10^{-6}M$ solution of $^{125}I$-labelled tailed cyclic peptide in 100 mM $NaH_2PO_4$ pH 6.0 (2 ml/sample). Samples were washed 3×5 min with 100 mM $NaH_2PO_4$ pH 6.0 and 3×5 min with $H_2O$. The radioactivity associated to each individual sample was counted by liquid scintillation counting and was reported to the surface of the sample to determine the amount of iodomated tailed cyclic peptide grafted by surface unity (picomol of peptide grafted/$cm^2$) (FIG. 3). The results obtained show an increased grafting of the peptide when a covalent attachment is performed using SMCC on aminated PET films compared to simple adsorption on aminated PET or coupling on native (unmodified) PET films.

EXAMPLE 3

Figure 4A:
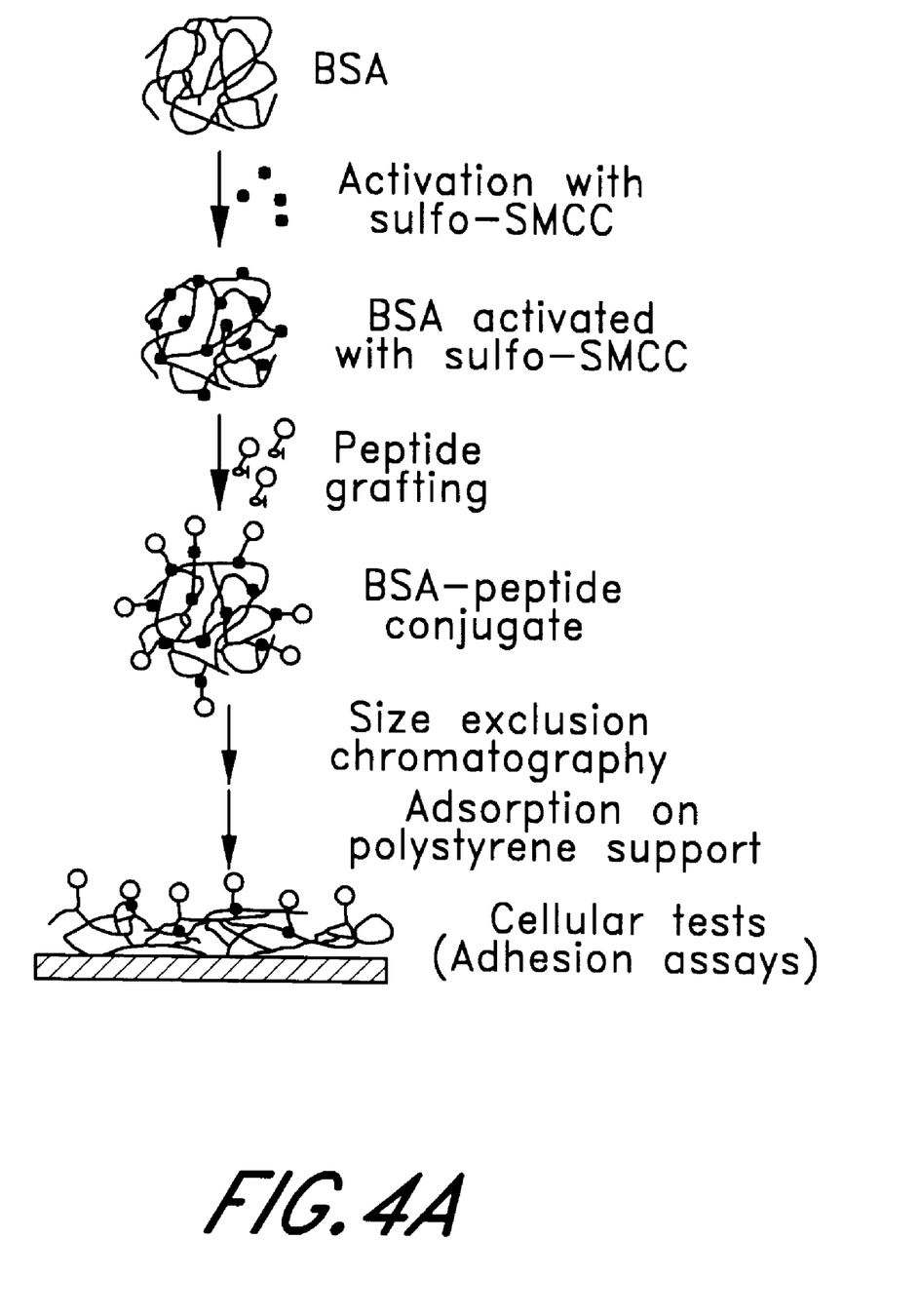
Figure 4B:
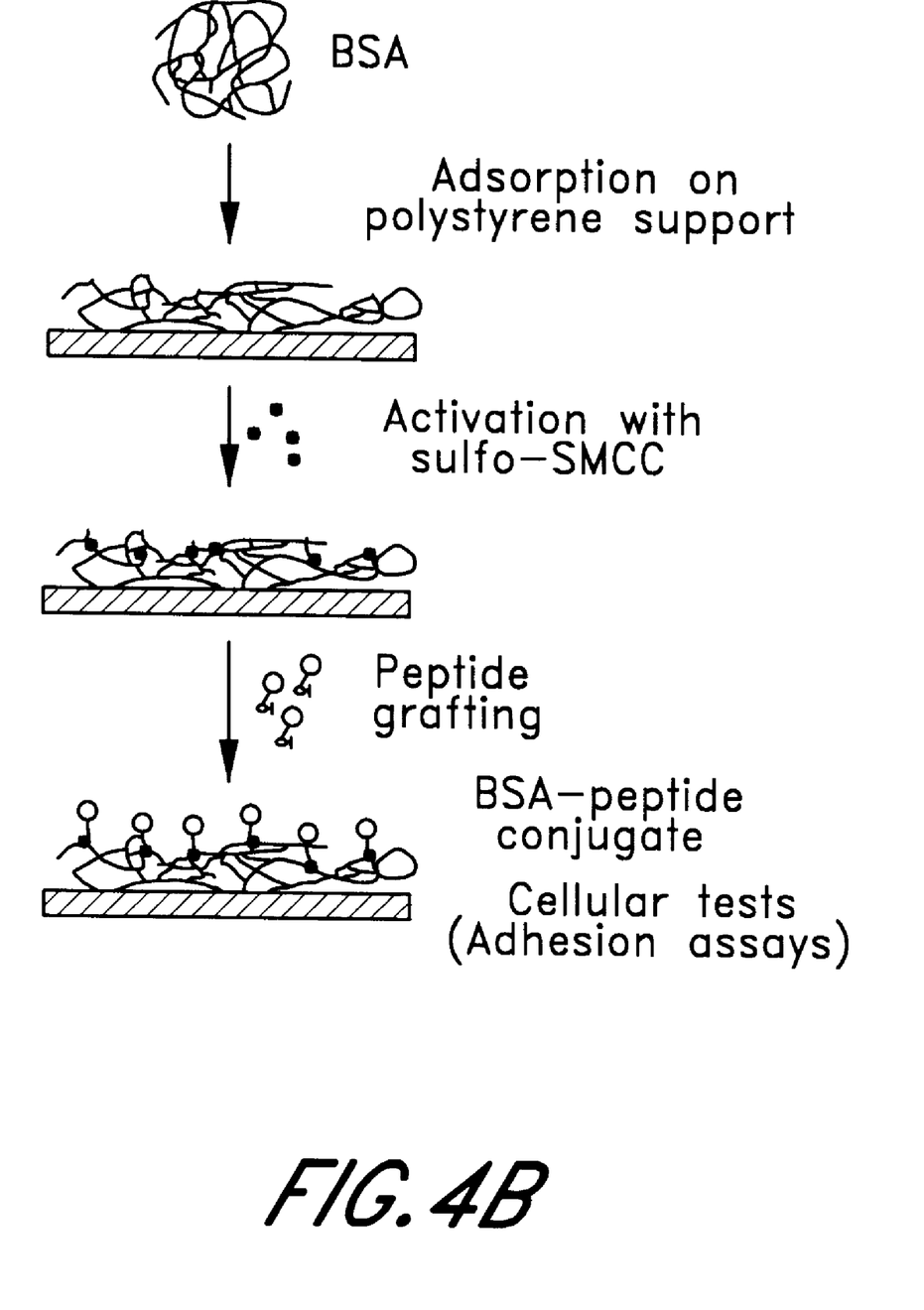

Enhancement of Cell Adhesion on Polystyrene Microwells Coated with Bovine Serum Albumin (BSA) Bearing Tailed Cyclic Peptides Containing the Arg-Gly-Asp (RGD) Sequence In the first experiment, the wells of a 96-wells polystyrene microwells plate were coated with bovine serum albumin already grafted with a RGD tailed cyclic peptide before testing the adherence of these coated plates (FIG. 4A). Albumin was activated with the heterobifunctional reagent sulfo-succinimidyl 4-(N-maleimidomethyl) cyclohexane-1-carboxylate i.e. sulfo-SMCC, to introduce reactive maleimido groups at the surface of the protein. BSA (8 mg/ml) was incubated in 100 mM $NaH_2PO_4$ pH 7.2 during 1 h at room temperature in the presence of sulfo-SMCC at a fmal concentration of 1.8 mg/ml. The solution was desalted and reconcentrated at 1 mg/ml on Amicon PM10. The activated BSA was then incubated overnight at room temperature in the presence of cyclo[-D-Val-Arg-Gly-Asp-Glu(-εAhx-Tyr-Cys-$NH_2$)-] (SEQ ID NO:17) at a concentration of 1.6 mg/ml. The BSA-peptide conjugate was desalted and reconcentrated at 1 mg/ml. The wells of a polystyrene microwell plate were then coated with this conjugate by incubation of 100 ml/well during 60 min, before washing two times with PBS.

In the second experiment the wells were coated with native bovine serum albumin which was then grafted with the tailed cyclic RGD peptide (FIG. 4B). The wells of a 96-well polystyrene microwell plate were first coated with bovine serum albumin (BSA) by incubating the protein at a concentration of 1 mg/ml (100 ml/well) during 60 min in PBS buffer. The wells were then washed two times with PBS buffer before activation with succiniidyl-4-(N-maleimidomethyl)cyclohexane- 1-carboxylate (SMCC). SMCC was dissolved at a final concentration of 26 mg/ml in 100 mM $NaH_2PO_4$ pH 7.2 10% DMSO and incubated in BSA-activated microwells (100 ml/well) at room temperature during 60 min. The wells were then washed two times with 100 mM $NaH_2PO_4$ pH 7.2 to remove unreacted SMCC. The tailed cyclic peptide cyclo[-DVal-Arg-Gly-Asp-Glu(-εAhx-Tyr-Cys-$NH_2$)] (SEQ ID NO: 17) at a concentration of 0.18 mg/ml in 100 mM $NaH_2PO_4$ pH 7.2 (100 ml/well) was incubated in the microwells overnight at room temperature. The wells were washed two times with phosphate buffer to remove the excess of peptide (unreacted). In a last experiment BSA was adsorbed on the plates as above and then incubated in the presence of the peptides for 15 h before washing and to performed the adhesion experiment with the cells.

Cell adhesion assays were performed on 96-well polystyrene plates coated with BSA bearing pro-adhesive Arg-Gly-Asp (RGD)-containing tailed cyclic peptides. Endothelial cells in MCDB were incubated 15 min at 37° C., then washed two times with PBS buffer. Adhesion of the cells in the wells was estimated by the colorimetric method of Givens K. T. et al (1990, Invest. Ophtalmol. Visual Sci., 31, 1856–1862) by measuring the absorbance at 405 nm of the para-mitrophenol liberated after incubating para-nitrophenol-N-acetyl-B-D-glucosaminidine. In both experiments, the results presented in FIGS. 5 and 6 showed an increased cell adhesion on polystyrene coated with BSA bearing the RGD tailed cyclic peptide compared to unmodified polystyrene or polystyrene coated with BSA. Control experiments were performed with BSA bearing cysteine residues grafted via SMCC (negative control) or with linear peptide, or with a random RGD peptide, or with fibronectin adsorbed on polystyrene support (positive control). The results showed better cell adhesion obtained for the adsorption of BSA bearing RGD tailed cyclic peptides than for the adsorption of the pro-adhesive protein fibronectin.

What is claimed is:

1. A cyclic peptide comprising a dicarboxylic amino acid and at least one tail for coupling to a second agent, wherein said cyclic peptide comprises four or more amino acids.

2. The cyclic peptide of claim 1, wherein said second agent comprises a solid support.

3. The cyclic peptide of claim 1, wherein said second agent comprises a compound having a molecular weight of at least 5 kDa.

4. The cyclic peptide of claim 3, wherein said compound having a molecular weight of at least 5 kDa is a protein.

5. The cyclic peptide of claim 1, wherein said second agent comprises at least one molecule of a second cyclic peptides.

6. The cyclic peptide of claim 1, wherein the dicarboxylic amino acid is an amino acid of the D or L conformation selected from the group consisting of glutamic acid and 2-aminoadipic acid.

7. The cyclic peptide of the claim 1, wherein the tail comprises amino acids.

8. The cyclic peptide of claim 7, wherein the amino acids are separated by a plurality of organic compounds having the formula -NH2-alkyl-COOH- or NH2-aryl-COOH.

9. The cyclic peptide of claim 7, wherein the amino acids of the tail are selected from the group consisting of cysteine, lysine, aspartic acid and glutamic acid.

10. The cyclic peptide of claim 8, wherein the amino acids of the tail include amino acids selected from the group consisting of cysteine, lysine, aspartic acid and glutamic acid.

11. The cyclic peptide of claim 8, wherein the organic compound is a 6-amino-hexanoyl.

12. The cyclic peptide according to claim 1, comprising a peptidic sequence that mimics the binding sequence of vascular endothelial growth factor (VEGF).

13. The cyclic peptide of claim 12, wherein said peptide sequence is EQIMRIKPHQ.

14. A method of preparing a cyclic peptide that comprises a dicarboxylic amino acid and at least one tail for coupling to a second agent, wherein said tail comprises amino acids, said method comprising the steps of:

synthesizing a peptide on a solid support or a high molecular weight compound;

cyclizing said peptide; and cleaving said peptide from the solid support, thereby obtaining the cyclic peptide.

15. The method of claim 14, wherein the synthesizing step is conducted using an automated peptide synthesizer.

16. The method of claim 15, additionally comprising a washing step between the synthesizing step and the cyclizing step.

17. The method of claim 16, wherein said washing step comprises washing with dichloromethane as a solvent in the presence of an aminated base.

18. The method of claim 16 wherein the washing step comprises a palladium wash.

19. The method of claim 14, additionally comprising a step of allyl cleavage between the synthesizing step and the cyclizing step.

20. The cyclic peptide of claim 1, wherein said cyclic peptide comprises between four and fifteen amino acids.

21. The cyclic peptide according to claim 5, comprising a peptidic sequence that mimics the binding sequence of vascular endothelial growth factor (VEGF).

* * * * *